US008920465B2

(12) United States Patent
Raju

(10) Patent No.: US 8,920,465 B2
(45) Date of Patent: Dec. 30, 2014

(54) NEEDLE-ELECTRODE AND TISSUE ANCHOR SYSTEM

(75) Inventor: Gottumukkala S. Raju, League City, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 738 days.

(21) Appl. No.: 12/519,624

(22) PCT Filed: Jan. 9, 2008

(86) PCT No.: PCT/US2008/050553
§ 371 (c)(1),
(2), (4) Date: Jun. 17, 2009

(87) PCT Pub. No.: WO2008/088982
PCT Pub. Date: Jul. 24, 2008

(65) Prior Publication Data
US 2010/0094341 A1    Apr. 15, 2010

Related U.S. Application Data

(60) Provisional application No. 60/885,113, filed on Jan. 16, 2007.

(51) Int. Cl.
*A61B 17/04* (2006.01)
*A61B 18/14* (2006.01)
*A61B 17/00* (2006.01)
*A61B 17/06* (2006.01)
*A61B 17/22* (2006.01)
*A61B 18/00* (2006.01)
*A61B 19/00* (2006.01)

(52) U.S. Cl.
CPC ......... *A61B 17/0401* (2013.01); *A61B 18/1477* (2013.01); *A61B 17/0469* (2013.01); *A61B 17/0487* (2013.01); *A61B 2017/00876* (2013.01); *A61B 2017/0404* (2013.01); *A61B 2017/0409* (2013.01); *A61B 2017/0445* (2013.01); *A61B 2017/0464* (2013.01); *A61B 2017/061* (2013.01); *A61B 2017/22038* (2013.01); *A61B 2018/00273* (2013.01); *A61B 2019/462* (2013.01)
USPC ............................ 606/232; 606/139; 606/167

(58) Field of Classification Search
CPC ................... A61B 2017/0409; A61B 17/0401; A61B 2017/0458; A61B 2017/0417; A61B 2017/0496; A61B 2017/0414; A61B 17/0469; A61B 17/0464; A61B 18/1477; A61F 2/0811
USPC ......... 606/139, 144–149, 151, 222–227, 232, 606/22, 161, 215, 216, 228–231
See application file for complete search history.

(56) References Cited

U.S. PATENT DOCUMENTS 5,549,631 A * 8/1996 Bonutti .......................... 606/232
5,626,614 A * 5/1997 Hart .............................. 606/232
(Continued)

FOREIGN PATENT DOCUMENTS

WO    2006037639    4/2006

OTHER PUBLICATIONS

Jae Seung Oh, International Search Report for International Patent Application No. PCT/US2008/050553, Korean Intellectual Property Office, dated Apr. 24, 2008.

(Continued)

*Primary Examiner* — Katherine M Shi
(74) *Attorney, Agent, or Firm* — Wong, Cabello, Lutsch, Rutherford & Brucculeri, LLP

(57) ABSTRACT

The disclosure provides a needle-electrode anchor system having a needle and an optional electrode with one or more anchors. The system can provide an electrical cutting current to the needle-electrode to create an opening in a tissue portion. An anchor coupled to the needle-electrode can be pushed through the opening with a pusher and pulled into position to set the anchor on a distal surface of the opening. If the tissue portion is to be approximated to another tissue portion, the system can be relocated to another tissue portion and another opening created with the cutting current with another anchor pushed through the opening and secured on a distal surface. Lines coupled to the anchors can be pulled together, approximating the tissue portions. If the tissue portion is to be retracted, an anchor line can be grasped to retract the tissue portion from an adjacent tissue portion.

15 Claims, 7 Drawing Sheets

(56) References Cited

U.S. PATENT DOCUMENTS

| | | |
|---|---|---|
| 5,667,513 A | 9/1997 | Torrie et al. |
| 5,718,717 A | 2/1998 | Bonutti |
| 7,004,959 B2 | 2/2006 | Bonutti |
| 2001/0041916 A1* | 11/2001 | Bonutti .................. 606/232 |
| 2004/0006352 A1* | 1/2004 | Nobles et al. .................. 606/144 |
| 2004/0082945 A1* | 4/2004 | Clague et al. .................. 606/32 |
| 2005/0033277 A1* | 2/2005 | Clague et al. .................. 606/32 |
| 2005/0165444 A1* | 7/2005 | Hart et al. .................. 606/213 |
| 2005/0261710 A1 | 11/2005 | Sakamoto et al. |
| 2005/0267533 A1* | 12/2005 | Gertner .................. 606/232 |
| 2006/0030884 A1* | 2/2006 | Yeung et al. .................. 606/232 |
| 2007/0055225 A1* | 3/2007 | Dodd et al. .................. 606/34 |
| 2010/0036395 A1* | 2/2010 | Miller .................. 606/139 |

OTHER PUBLICATIONS

Jae Seung Oh, Written Opinion for International Patent Application No. PCT/US2008/050553, Korean Intellectual Property Office, dated Apr. 24, 2008.

* cited by examiner

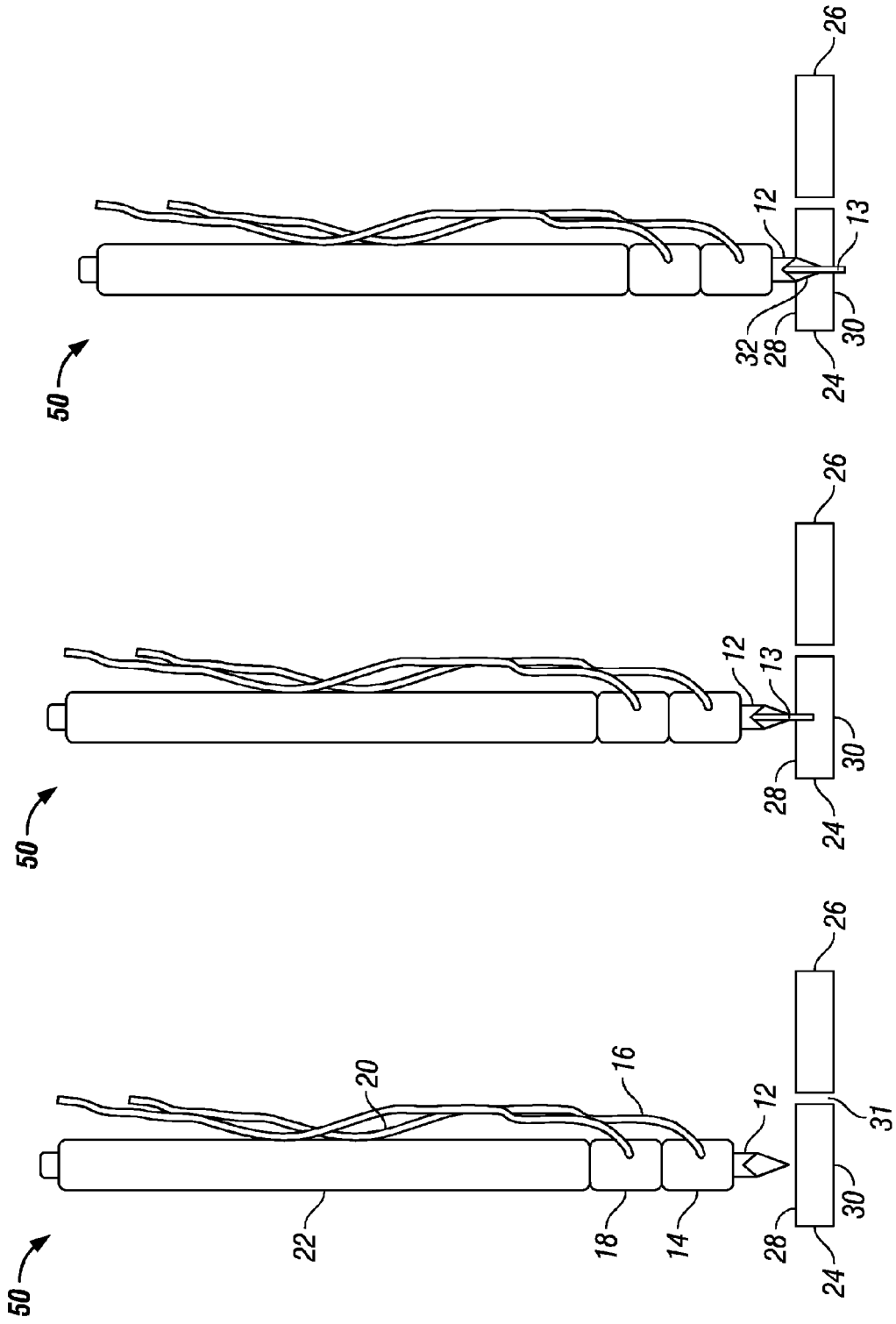

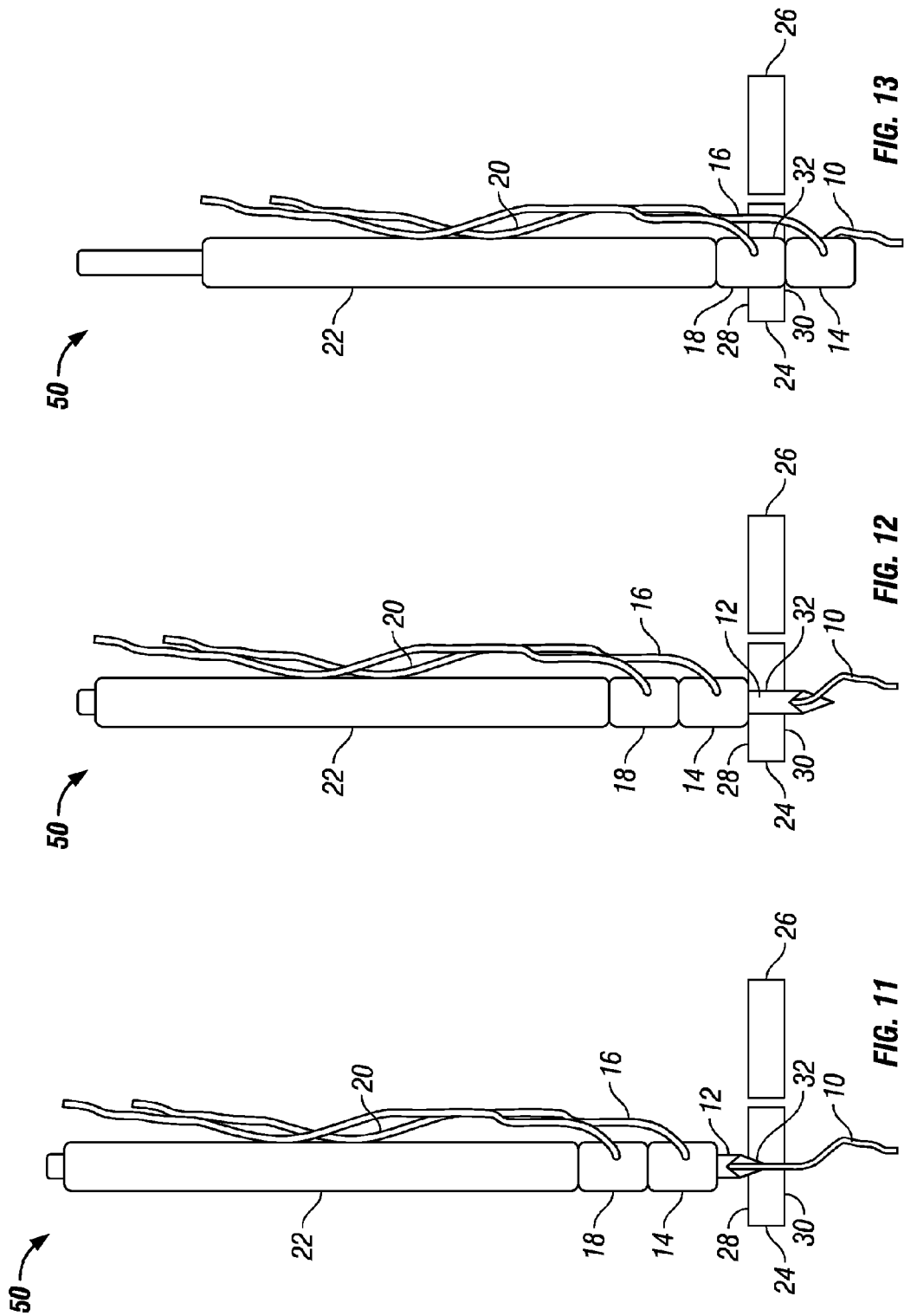

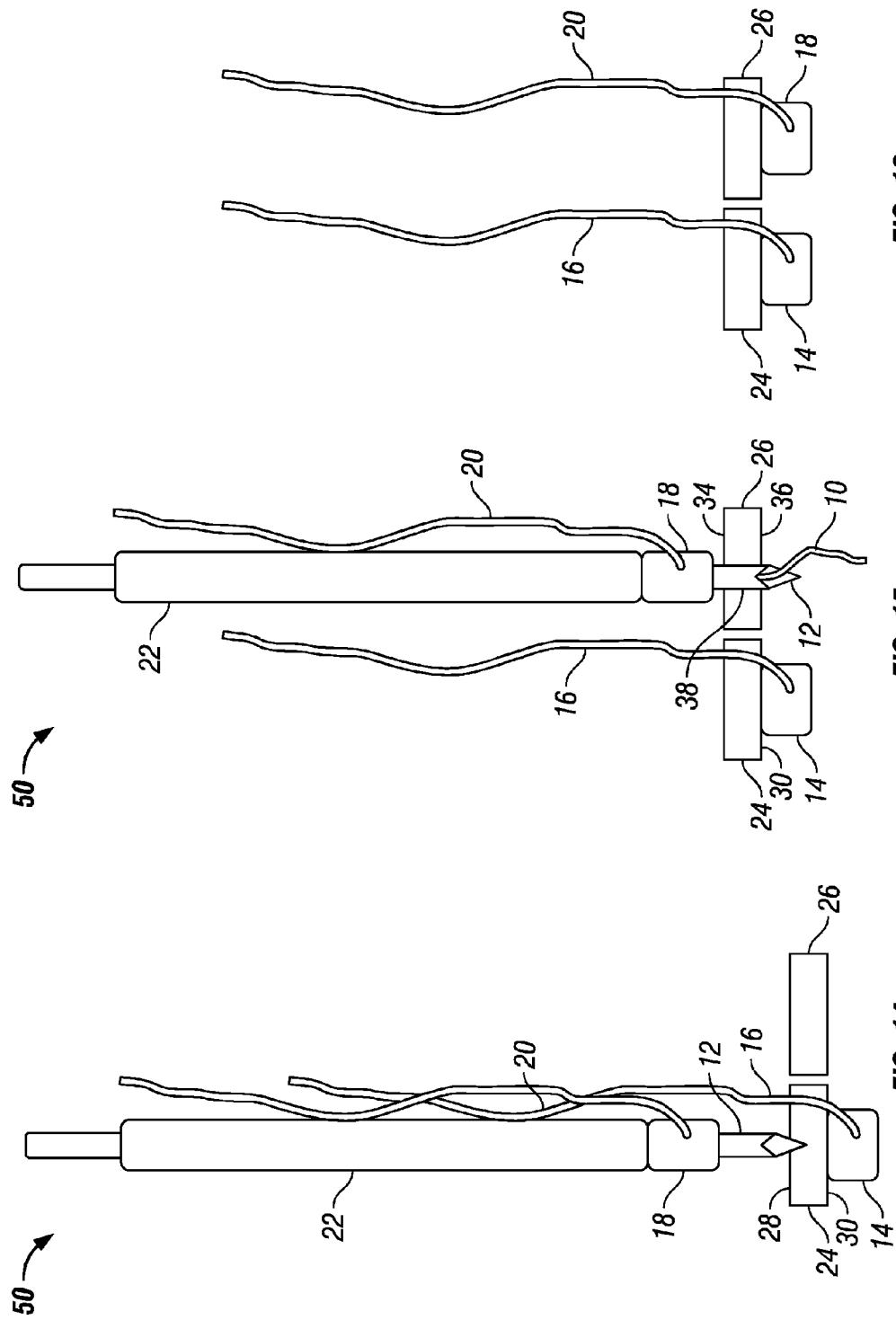

NEEDLE-ELECTRODE AND TISSUE ANCHOR SYSTEM

CROSS REFERENCE TO RELATED APPLICATIONS

The application is a national stage application under 35 U.S.C. §371 of PCT/US2008/050553, filed Jan. 9, 2008, which claims the benefit of U.S. Provisional Appl. No. 60/885,113, filed Jan. 16, 2007.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO APPENDIX

Not applicable.

BACKGROUND

1. Field of the Invention

The present disclosure medical procedures. More particularly, the disclosure relates to setting tissue anchors for tissue approximation and retraction in medical procedures.

2. Description of Related Art

During medical procedures on tissues surfaces, it is often desirable to pull tissue portions toward each other, generally known as "approximation". For example, the tissue portions can be adjacent to a wound that needs suturing or other closure. The gap between adjacent sides of the wound may be so large as to make the closure tenuous and time consuming. Other medical procedures often benefit from pulling tissue portions away from each other, known as "retraction." The tissue surfaces may benefit from such retraction for medical diagnosis, enhanced viewing and placement during surgical removal, and other medical procedures.

Known medical instruments, such as surgical hemostats and dressing forceps are routinely used for such procedures external to a body of an organism. However, the current endoscopic, laparoscopic, and other medical procedures performed internally to the body create an order of magnitude in complexity. The limited viewing and access during these internal procedures typically prohibit the use of such known instruments for tissue approximation and retraction. The size of the typical instruments is prohibitive for the internal procedures, but more importantly most procedures need to be done with one instrument inserted into the area.

When closing a gap after an excision or created by a wound, an internally inserted and actuated surgical clip can close a relatively small gap through its known mechanisms by the same instrument inserted into the area. However, a gap that exceeds the capabilities of the clips needs special and time consuming efforts to close. One known method is to start at one end of the gap and slowly close small sections progressively to the other end of the gap with a large number of clips, similar to the operation of a zipper. One recent procedure required about five hours to excise and close a 5 cm tumor.

To approximate large gaps in tissues or retract the tissues often requires inserting an anchor through the wall of the body portion, such as an abdominal wall, where a line, such as a suture, is attached to the anchor. The line can be pulled toward another anchor and line in another portion of the tissue to approximate the respective tissue portions, or toward another portion of the body to retract the tissue portion with the anchor away from an adjacent tissue portion. A needle with an anchor is used to push through the wall and locate the anchor on a distal side of the wall. However, inserting the anchor through the wall can be technically challenging due to the thickness of some portions of the wall. A significant amount of force is needed to push the needle and anchor through the wall and often bends the flexible endoscope or other scope through which the needle is inserted. The amount of force complicates the procedure and at time requires placement of the anchor to a less desirable location.

Thus, there remains a need for an improved method and device to insert an anchor into a tissue portion to approximate and retract the tissue portion.

BRIEF SUMMARY

In this field, special and sometimes simple devices from the viewpoint of hindsight can yield major improvements in costs, time, or the ability to even perform a desired medical procedure. The present disclosure provides an improved method and device for better inserting of an anchor into a tissue portion for approximation and retraction of a tissue portion during a medical procedure.

The disclosure provides a needle-electrode anchor system having a needle and an optional electrode with one or more anchors. The system can provide an electrical cutting current to the needle-electrode to create an opening in a tissue portion. An anchor slidably coupled to the needle-electrode can be pushed through the opening with a pusher and then pulled into position to set the anchor on a distal surface of the opening. If the tissue portion is to be approximated to another tissue portion, the system can be relocated to another tissue portion and another opening created with the cutting current with another anchor pushed through the opening and secured on a distal surface. Lines coupled to the anchors can be pulled together, approximating the tissue portions. If the tissue portion is to be retracted, an anchor line can be grasped to retract the tissue portion from an adjacent tissue portion.

The disclosure also provides a needle-electrode anchor system, comprising: a needle; at least one anchor coupled to the needle, the anchor being coupled to a line; and a pusher catheter coupled to the needle and adapted to push the anchor off of the needle and at least partially through a tissue portion.

The disclosure further provides a method of adjusting a location of a first tissue portion relative to a second tissue portion with a needle-electrode anchor system having a needle and at least one anchor coupled to the needle, the anchor being coupled to a line, comprising: creating an opening through a first surface of the first tissue portion with the needle; pushing the anchor through the opening and off of the needle; and securing the anchor on a second surface of the first tissue portion distal from the first surface relative to the tissue portion.

BRIEF DESCRIPTION OF THE DRAWINGS

While the concepts provided herein are susceptible to various modifications and alternative forms, only a few specific embodiments have been shown by way of example in the drawings and are described in detail below. The figures and detailed descriptions of these specific embodiments are not intended to limit the breadth or scope of the concepts or the appended claims in any manner. Rather, the figures

FIG. 8 is a schematic diagram of the anchor assembly in proximity to a first surface of a first tissue portion.

FIG. 9 is a schematic diagram of the anchor assembly having a needle with an optional electrode extending from the needle forming an opening in the first tissue portion.

FIG. 10 is a schematic diagram of the anchor assembly having a needle with the optional electrode extending from the needle forming an opening through the first tissue portion to a distal surface of the first tissue portion.

FIG. 11 is a schematic diagram of the anchor assembly with a guide wire inserted through the opening formed by the needle-electrode.

FIG. 12 is a schematic diagram of the anchor assembly with the needle inserted through the opening along a path provided by the guide wire inserted through the opening.

FIG. 13 is a schematic diagram of the anchor assembly with a pusher catheter pushing a first anchor through the opening formed by the needle.

FIG. 14 is a schematic diagram of the anchor assembly retracted from the opening with an anchor disposed on a distal surface of the opening.

FIG. 15 is a schematic diagram of the anchor assembly similarly forming a second opening in a second tissue portion.

FIG. 16 is a schematic diagram of the anchor assembly with the pusher pushing a second anchor through the second opening in the second tissue portion formed by the needle-electrode.

DETAILED DESCRIPTION

One or more illustrative embodiments of the concepts disclosed herein are presented below. Not all features of an actual implementation are described or shown in this application for the sake of clarity. It is understood that the development of an actual embodiment, numerous implementation-specific decisions must be made to achieve the developer's goals, such as compliance with system-related, business-related and other constraints, which vary by implementation and from time to time. While a developer's efforts might be complex and time-consuming, such efforts would be, nevertheless, a routine undertaking for those of ordinary skill in the art having benefit of this disclosure.

Figure 1:
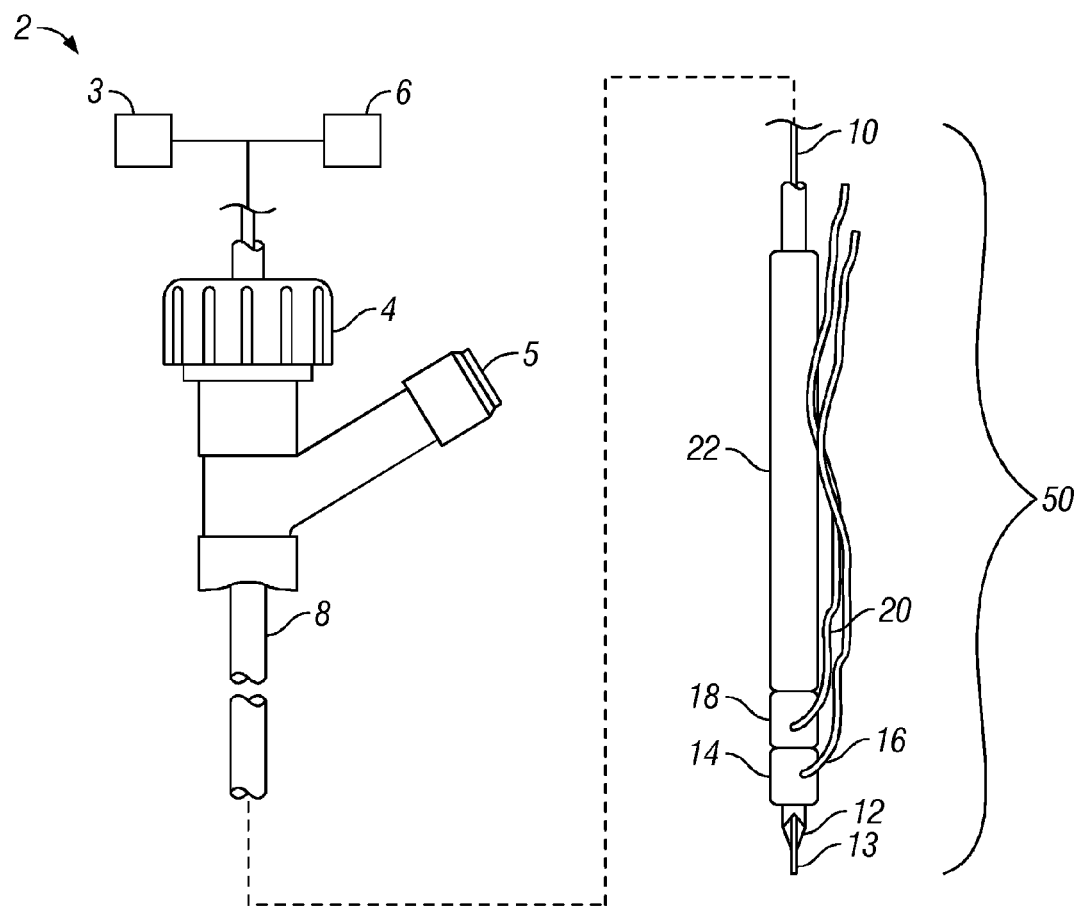
FIG. 1 is a schematic diagram of a needle-electrode anchor system.

FIG. 1 is a schematic view of an exemplary embodiment of a needle-electrode anchor system. Without limitation, the needle-electrode anchor system can be particularly useful in gastrointestinal surfaces, such as abdominal walls, colon, esophageal tissues, and other tissue portions having walls that are accessible with scopes. The endoscope system 2 generally includes an endoscope assembly 4, as is known to those with ordinary skill in the art. An endoscope assembly 4 of varying sizes can be inserted through portions of a body to illuminate and remotely view portions of the body through which the endoscope assembly is inserted. A side injection port 5 is used to insert various catheters, tools, and other assemblies with the endoscope assembly 4. The endoscope assembly 4 can be a single channel endoscope or a multi-channel endoscope having two or more channels. Most practitioners use single-channel endoscopes due to their simplicity and lower cost. Thus, one embodiment of the present disclosure uses a single channel endoscope. Other embodiments can use multi-channel endoscopes as desired. The term "endoscope" is used broadly in this application and includes any tool insertable into a body having a channel through which tools and other devices can be placed and used, whether inserted through a natural body orifice or through an artificially created opening, such as through an incision or other procedure, and thus includes a laparoscope and other medical scopes modified to be able to convey tools and related instruments for purposes described herein.

The endoscope assembly 4 generally includes a monitor and lens system 3 for viewing the distal end of the endoscope as it is inserted into the body and guided to the desired location. When a distal lens is unavailable, known imaging techniques external to the body can be used for locating the tools internal to the body. Further, the endoscope assembly 4 includes a light and power source 6 for providing illumination to the endoscope to view the relevant tissues, powering the needle-electrode system described herein, and providing energy to other sources of light or power in the system. The system 2 can include an endoscope 8 for inserting into the body as a channel for delivery of elements described herein and can be used for viewing remotely the relevant tissues for the one or more anchors. A guide wire 10 can be disposed along the endoscope 8 through a channel formed in the endoscope as is known to those in the art.

The system 2 includes an anchor assembly 50. The anchor assembly 50 generally includes a needle 12 and optionally an electrode 13 suitable for receiving a voltage and forming an opening through electrical current in conjunction with the needle tip. The assembly 50 also includes at least a first anchor 14 with a line 16 coupled thereto and in some embodiments a plurality of anchors, such as a second anchor 18 and a line 20 coupled thereto. A pusher catheter 22 is slidably coupled to the needle in proximity to at least one anchor to push the anchor into position, as described herein.

The needle 12 can be disposed through the endoscope 8. The anchors 14, 18 and the pusher catheter 22 can be disposed over the endoscope. When the endoscope 8 is directed to the proper location, and the needle-electrode has formed one or more openings through the tissue portion in question, the pusher catheter can push the anchor through the opening to the distal side of the tissue portion.

Figure 4:
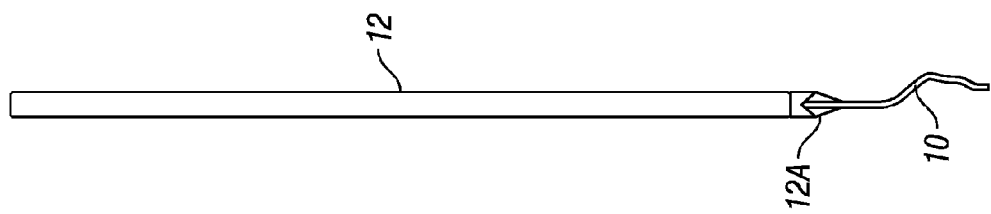
FIG. 4 is a schematic diagram of the needle-electrode system with a guide wire extending from the needle.
Figure 3:
FIG. 3 is a schematic diagram of the needle with an electrode inserted therein.
Figure 2:
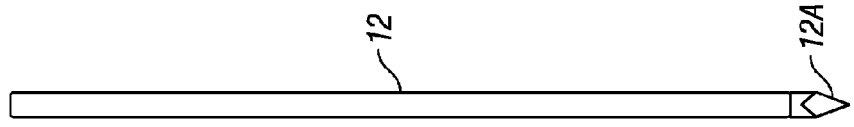
FIG. 2 is schematic diagram of an exemplary needle of the anchor system.
Figure 7:
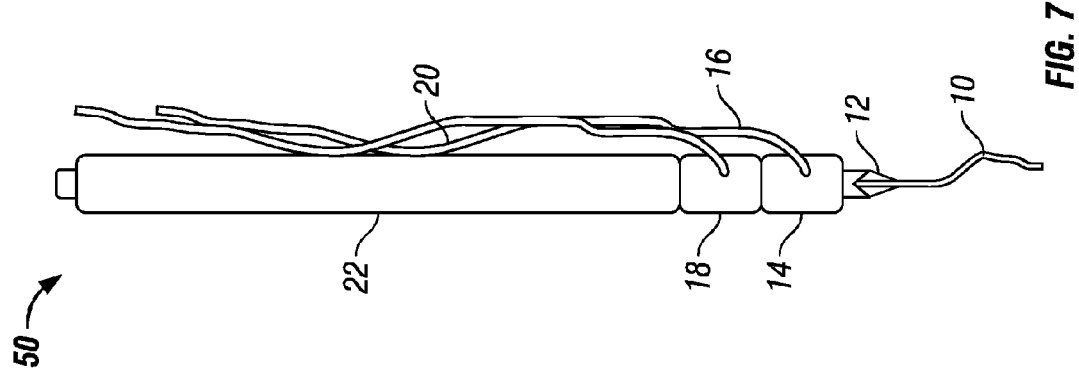
FIG. 7 is a schematic diagram of the needle-electrode system with a guide wire and a first anchor with a line attached thereto, a second anchor with a corresponding line, and a pusher catheter inserted adjacent the second anchor as an anchor assembly.
Figure 6:
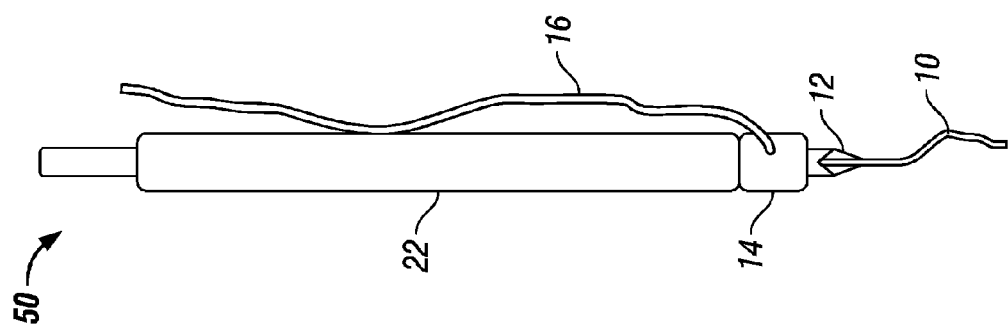
FIG. 6 is a schematic diagram of the needle-electrode system with a guide wire and a first anchor with a line attached thereto and a pusher inserted adjacent the anchor.
Figure 5:
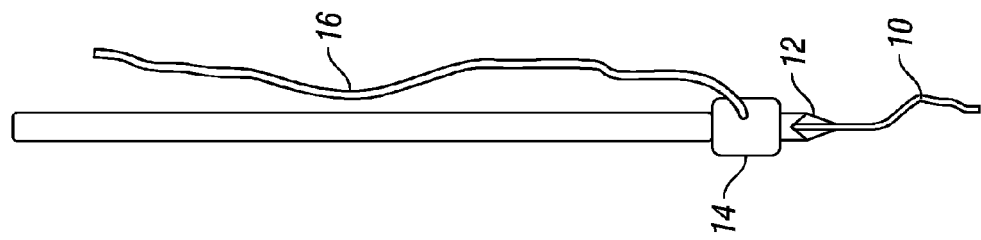
FIG. 5 is a schematic diagram of the needle-electrode system with a guide wire and a first anchor with a line attached thereto.

FIGS. 2-7 illustrate an exemplary anchor assembly and the figures will be described in conjunction with each other. FIG. 2 is schematic diagram of an exemplary needle of the anchor system. FIG. 3 is a schematic diagram of the needle with an electrode inserted therein. FIG. 4 is a schematic diagram of the needle-electrode system with a guide wire extending from the needle. FIG. 5 is a schematic diagram of the needle-electrode system with a guide wire and a first anchor with a line attached thereto. FIG. 6 is a schematic diagram of the needle-electrode system with a guide wire and a first anchor with a line attached thereto and a pusher catheter inserted adjacent the anchor. FIG. 7 is a schematic diagram of the needle-electrode system with a guide wire and a first anchor with a line attached thereto, a second anchor with a corresponding line, and a pusher catheter inserted adjacent the second anchor as an anchor assembly.

FIG. 2 illustrates a needle having an aperture 12A through which fluid or one or more elements can be disposed therethrough. The needle 12 can be any appropriate gauge needle such as without limitation, gauges 18-26. The needle can be a non-energized needle or an energized needle. For an energized needle, as shown in FIG. 3, an electrode 13 can be one of the elements disposed through the needle 12. The electrode 13 can extend beyond the tip of the needle and to which a cutting current can be applied such as is used in an electrocautery needle. The cutting current can be any variety of currents as may be appropriate to cutting through the tissue. Generally, an arc is formed between the electrode and the tip of the needle to produce a heated zone that is able to cut through the tissue as described herein.

As shown in FIG. 4, a guide wire 10 can be disposed through the needle 12, specifically through the opening 12A, generally after the electrode 13 is removed from the needle. If the opening 12A in the needle 12 is sufficiently large, the electrode 13 and the guide wire 10 can be disposed concurrently therethrough. If the opening 12A is sized to allow only one, then the electrode can be removed after cutting and the guide wire 10 inserted therefor. In some embodiments, the electrode 13 and the guide wire 10 can be combined. For example, the guide wire 10 can be insulated except at the tip and act as the electrode 13 for cutting the tissue portion and then be extended to act as the guide wire.

As shown in FIG. 5, at least one anchor 14 can be disposed on or around the needle 12. The anchor 14 (and anchor 18 described below) can be any suitable shape, including without limitation, a hemi-circumferential element that hugs the needle electrode. Further, the anchor 14 can be split, spliced, circumferential, or other shapes as may be appropriate for the situation. The material of the anchor can be any bio-compatible material including without limitation, bio-reabsorbable, plastic, metal, magnetic, inert, therapeutic, and other materials suitable for the application intended. Further, the anchor can be a mesh material. The anchor can maintain a rigid shape after installation or conform to various shapes, including a cross-sectionally enlarged but thinner disk compared to anchor dimensions prior to installation to provide more surface contact with the tissue portion.

A line 16, such as a thread, wire, or other elongated element, can be coupled to the anchor 14. In at least one embodiment, the line 16 forms a suture that can be coupled to an adjacent suture to pull tissue portions toward each other, As shown in FIG. 6, a pusher catheter 22 can be disposed around the needle 12 adjacent to the anchor 14. A pusher catheter 22 is known to those with ordinary skill in the art and used for other purposes. While the pusher catheter and the anchor are schematically shown around the needle 12, it is to be understood that the pusher catheter and anchor may actually be directly attached around an endoscope 8, illustrated in FIG. 1, in which the needle 12 is placed. As shown in FIG. 7, the assembly 50 can include a plurality of anchors. For example, the anchor 14 can be disposed adjacent a second anchor 18 with a line 20 coupled thereto. The pusher catheter 22 can be exposed adjacent to the second anchor 18. A sheath (not shown) can surround the pusher catheter and one or more anchors.

FIGS. 8-17 illustrate one exemplary and non-limiting method of using the needle-electrode anchor system 2 described above. It is to be understood that variations are possible, including one to several anchors disposed on the anchor assembly 50. FIG. 8 is a schematic diagram of the anchor assembly in proximity to a first surface of a first tissue portion. The anchor assembly 50 can be disposed down the endoscope to a desired location on a first tissue portion 24. The first tissue portion 24 includes a first surface 28 and a second surface 30 on an opposite face of the first tissue portion, that is, distal from the first surface relative to the tissue portion. The first tissue portion 24 can be separated from a second tissue portion 26 by a gap 31. In at least one embodiment, the anchor assembly 50 can be used to pull two or more tissue portions toward each other. It is to be understood that the same anchor assembly 50 can be used to retract one or more tissue portions away from the other, such as to allow for excision of lesions and other procedures where tissue retraction is appropriate. Thus, a similar sequence could be followed with simply a different end result.

FIG. 9 is a schematic diagram of the anchor assembly having a needle with an optional electrode extending from the needle forming an opening in the first tissue portion. An electrode 13 can be disposed through the needle 12 and cutting current applied thereto. The electrode can cut into the first tissue portion 24 starting at the first surface 28.

FIG. 10 is a schematic diagram of the anchor assembly having a needle with the optional electrode extending from the needle forming an opening 32 through the first tissue portion 24 to a distal surface of the first tissue portion. As shown in FIG. 10, the cutting can continue until at least the electrode 13, if used, has pierced the first tissue portion 24 to the second surface 30 distal from the first surface. If the electrode 13 is not used, the needle 12 can be used to at least partially create the opening in the tissue portion without the cutting current.

FIG. 11 is a schematic diagram of the anchor assembly with a guide wire inserted through the opening formed by the needle-electrode. As shown in FIG. 11, a guide wire 10 can be disposed through the needle 12 and pass through the opening 32. The electrode 13 can be removed prior to the guide wire being disposed through the needle, if appropriate. The guide wire 10 can be used to push organs and other tissues away from the immediate vicinity of the second surface 30 of the first tissue portion to allow subsequent anchor placement without interfering with the other tissues.

FIG. 12 is a schematic diagram of the anchor assembly with the needle inserted through the opening along a path provided by the guide wire inserted through the opening. As shown in FIG. 12, if the needle has not already been pushed through the first tissue portion 24, the needle can follow the guide wire 10 and be pushed through the first tissue portion 24 using the opening 32 formed by the needle-electrode. For example, the first tissue portion 24 may be a greater thickness that might be appropriate to follow a longer guide wire extending from the needle.

FIG. 13 is a schematic diagram of the anchor assembly with a pusher catheter pushing a first anchor through the opening formed by the needle. The pusher catheter can push the first anchor 14 through the opening 32 formed at least partially through the first tissue portion 24, such as through the first surface 28, the internal layer or layers of the first tissue portion 24, and through the second surface 30.

FIG. 14 is a schematic diagram of the anchor assembly retracted from the opening with an anchor disposed on a distal surface of the opening. As shown in FIG. 14, the anchor assembly 50 can be retracted from the first tissue portion 24, leaving the anchor 14 disposed on the distal side of the first tissue portion 24 adjacent the second surface 30. The line 16 can be retained through the opening in the first tissue portion 24 on the proximal side of the anchor system 50 for later grasping and/or tying.

FIG. 15 is a schematic diagram of the anchor assembly similarly forming a second opening in a second tissue portion. Having disposed the first anchor 14 through the first tissue portion 24, the anchor system 50 can be relocated to a second tissue portion 26. The second tissue portion 26 can include, similar to the first tissue portion 24, a first surface 34 on the proximal side of the anchor assembly 50 and a second surface 36 distal from the first surface 34. The needle 12 with the optional electrode described above can use a cutting current to form an opening 38 through the second tissue portion 26. The needle 12 can follow the electrode described above or a guide wire 10 inserted through the needle and through the opening 38, so that the needle is disposed through the second tissue portion 26. While it has been described in the above figures that the needle 12 is disposed through the tissue portion 26, it is to be understood that in some embodiments, the anchor could be disposed through the opening created by the electrode and/or guide wire without necessarily puncturing through the tissue portions with the needle.

FIG. 16 is a schematic diagram of the anchor assembly with the pusher catheter pushing a second anchor through the second opening in the second tissue portion formed by the needle-electrode. The anchor assembly 50 can be retracted from the tissue portions after the pusher catheter 22 has pushed the second anchor 18 through the opening 38, leaving the line 20 on the proximal side of the pusher system 50.

Figure 17:
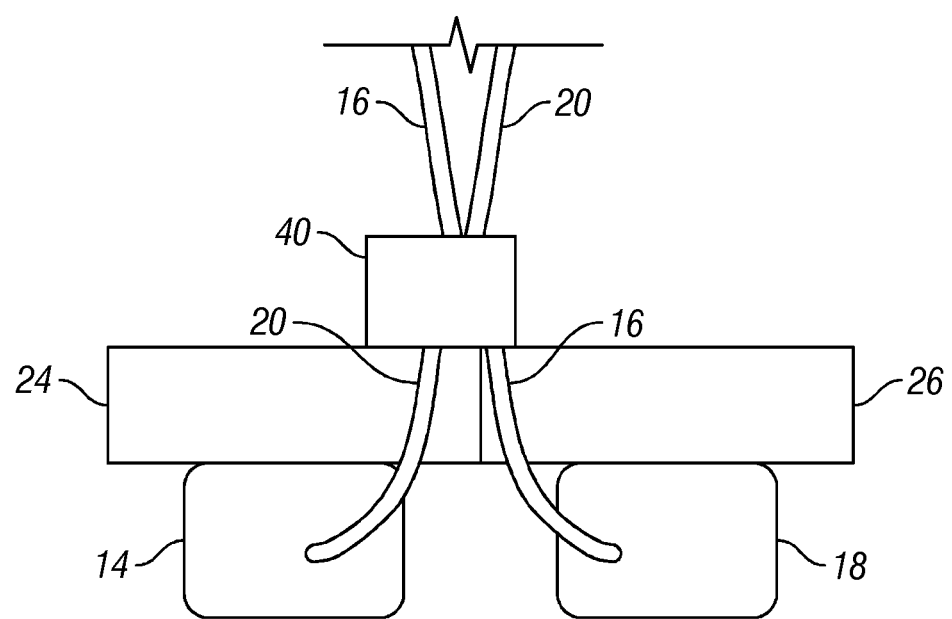
FIG. 17 is a schematic diagram of the first and second anchors tied together with a tie device to approximate the tissue portions with the anchors.

FIG. 17 is a schematic diagram of the first and second anchors tied together with a tie device to approximate the tissue portions with the anchors. As shown in FIG. 17, the lines 16, 20 coupled to the anchors 14, 18, respectively, can be attached and tied with a tie device 40, known to those with ordinary skill in the art. The tying can pull the first tissue portion 24 in close proximity to the second tissue portion 26 and reduce the gap 31 described above. The lines 16, 20 can be coupled to the anchors 14, 18, respectively, in a position that encourages rotation of the anchors from a longitudinal direction to a transverse direction relative to the openings in the respective tissues portions through which the anchors were pushed. This rotation allows the anchors to provide additional surface area contact with the tissue portions and reduce the possibility of erosion of the tissue portions and unintended displacement of the anchors. Further, anchors can be flexible and expand in cross-sectional area when pulled with the lines to provide the referenced additional surface area contact. Optionally, the one or more of the anchors 14, 18 and the tie device 40 can be include magnetic materials, so that the anchors and tie device are attracted from the opposite tissue surfaces.

As further described above, the anchor assembly can provide an anchor, such as anchor 14, in the first tissue portion and the line 16 be pulled to retract the first tissue portion 24 from the second tissue portion 26. Further, additional anchors could be disposed in other tissue portions for additional approximation or retraction of other tissue portions.

The invention has been described in the context of various embodiments and not every embodiment of the invention has been described. Apparent modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect all such modifications and improvements to the full extent that such falls within the scope or range of equivalent of the following claims.

The various methods and embodiments of the invention can be included in combination with each other to produce variations of the disclosed methods and embodiments, as would be understood by those with ordinary skill in the art, given the understanding provided herein. Also, various aspects of the embodiments could be used in conjunction with each other to accomplish the understood goals of the invention. Also, the directions such as "top," "bottom," "left," "right," "upper," "lower," and other directions and orientations are described herein for clarity in reference to the figures and are not to be limiting of the actual device or system or use of the device or system. The term "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, directly or indirectly with intermediate elements, one or more pieces of members together and can further include without limitation integrally forming one functional member with another in a unity fashion. The coupling can occur in any direction, including rotationally. Unless the context requires otherwise, the word "comprise" or variations such as "comprises" or "comprising", should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. Further, the order of steps can occur in a variety of sequences unless otherwise specifically limited. The various steps described herein can be combined with other steps, interlineated with the stated steps, and/or split into multiple steps. Additionally, the headings herein are for the convenience of the reader and are not intended to limit the scope of the invention.

Further, any references mentioned in the application for this patent as well as all references listed in the information disclosure originally filed with the application are hereby incorporated by reference in their entirety to the extent such may be deemed essential to support the enabling of the invention. However, to the extent statements might be considered inconsistent with the patenting of the invention, such statements are expressly not meant to be considered as made by the Applicant(s).

The invention claimed is:

1. A wound anchor system, comprising:
    a needle having a central opening and adapted to at least partially create an opening in a first tissue portion and an opening in a second tissue portion;
    at least a first anchor and a second anchor, each anchor being coupled to its own line, and each line separate from each other and unaffixed to any tie device when the anchors are pushed through the tissue portions such that the anchors are adapted to be separately manipulated if desired;
    a pusher catheter adapted to push the first anchor at least partially through the opening in the first tissue portion and adapted to push the second anchor at least partially through the opening in the second tissue portion, and an endoscope dimensioned and adapted to deliver the needle and the at least first and second anchors and pusher catheter, wherein the needle is disposed inside a channel of the endoscope and the at least first and second anchors and pusher catheter are slidably disposed on an outside of the endoscope, wherein the lines attached to the at least first and second anchors are adapted and configured to approximate the anchored tissue portions toward each other or retract the anchored tissue portions away from each other when the anchors are coupled with the respective tissue portions.

2. The system of claim 1, wherein at least one of the anchors is adapted to change orientation, shape, or a combination thereof after insertion at least partially through the tissue portion.

3. The system of claim 1, further comprising a cutting electrode dimensioned and adapted for passage through an inner channel of the needle.

4. The system of claim 1, further comprising a guide wire dimensioned and adapted for passage through an inner channel of the needle.

5. The system of claim 1, further comprising a sheath around the pusher catheter and the at least first and second anchors.

6. The system of claim 1, wherein at least one of the anchors is a mesh material.

7. The system of claim 1, wherein the at least first and second anchors are magnetic.

8. The system of claim 1, further comprising a line aggregator adapted and dimensioned to secure lines coupled to the anchors.

9. A wound closure system, comprising:
a needle adapted to at least partially create an opening in at least a first and second tissue portion;
a cutting electrode running through the needle and adapted to provide a cutting current to tissue portions;
at least a first anchor and a second anchor, each anchor being coupled to its own line, each line separate from each other and unaffixed to any tie device when the anchors are pushed through the tissue portions such that the anchors are adapted to be separately manipulated if desired;
a pusher catheter adapted to push the first anchor at least partially through the opening in the first tissue portion and adapted to push the second anchor at least partially through the opening in the second tissue portion, and
an endoscope dimensioned and adapted to deliver the needle and the at least first and second anchors and pusher catheter, wherein the needle is disposed inside a channel of the endoscope and the at least first and second anchors and pusher catheter are slidably disposed on an outside of the endoscope,
wherein the lines attached to the at least first and second anchors are adapted and configured to approximate the anchored tissue portions toward each other or retract the anchored tissue portions away from each other when the anchors are coupled with the respective tissue portions.

10. The system of claim 9, wherein at least one of the anchors is adapted to change orientation, shape, or a combination thereof after insertion at least partially through the tissue portion.

11. The system of claim 9, further comprising a guide wire dimensioned and adapted for passage through an inner channel of the needle.

12. The system of claim 9, wherein at least one of the anchors is a mesh material.

13. The system of claim 9, wherein at least one pair of anchors is magnetic.

14. The system of claim 9, further comprising a sheath around the pusher catheter and the at least first and second anchors.

15. The system of claim 9, further comprising a line aggregator adapted and dimensioned to secure the lines coupled to the anchors.

\* \* \* \* \*